US011360315B2

(12) United States Patent
Tu et al.

(10) Patent No.: US 11,360,315 B2
(45) Date of Patent: Jun. 14, 2022

(54) AUGMENTED REALITY EYEGLASSES HAVING STRUCTURED LIGHT DETECTING FUNCTION

(71) Applicant: Acer Incorporated, New Taipei (TW)

(72) Inventors: Tsung-Wei Tu, New Taipei (TW); Yi-Jung Chiu, New Taipei (TW); Shih-Ting Huang, New Taipei (TW); Yen-Hsien Li, New Taipei (TW)

(73) Assignee: Acer Incorporated, New Taipei (TW)

( * ) Notice: Subject to any disclaimer, the term of this patent is extended or adjusted under 35 U.S.C. 154(b) by 0 days.

(21) Appl. No.: 17/152,676

(22) Filed: Jan. 19, 2021

(65) Prior Publication Data

US 2022/0082830 A1 Mar. 17, 2022

(30) Foreign Application Priority Data

Sep. 17, 2020 (TW) ................. 109132019

(51) Int. Cl.
*G02B 27/01* (2006.01)
*G02B 27/00* (2006.01)
*A61B 3/107* (2006.01)

(52) U.S. Cl.
CPC .......... *G02B 27/0172* (2013.01); *A61B 3/107* (2013.01); *G02B 27/0093* (2013.01); *G02B 2027/0138* (2013.01); *G02B 2027/0178* (2013.01)

(58) Field of Classification Search
CPC ............ G02B 27/0172; G02B 27/0093; G02B 2027/0138; G02B 2027/0178; A61B 3/107
See application file for complete search history.

(56) References Cited

U.S. PATENT DOCUMENTS

| 9,069,164 | B2* | 6/2015 | Starner .................. G06F 3/017 |
| 10,209,517 | B2* | 2/2019 | Popovich ................ G02B 6/34 |
| 10,423,222 | B2* | 9/2019 | Popovich ........... G02B 27/0093 |
| 10,591,756 | B2* | 3/2020 | Popovich ............. G02F 1/1326 |
| 10,983,340 | B2* | 4/2021 | Popovich ................ G02B 6/00 |
| 2013/0278631 | A1* | 10/2013 | Border .................. G02C 5/143 |
| | | | 345/633 |
| 2018/0008141 | A1* | 1/2018 | Krueger .................. A61B 5/11 |

(Continued)

FOREIGN PATENT DOCUMENTS

| CN | 206696529 | 12/2017 |
| CN | 207488622 | 6/2018 |

(Continued)

*Primary Examiner* — Ricardo Osorio
(74) *Attorney, Agent, or Firm* — JCIPRNET

(57) ABSTRACT

Augmented reality eyeglasses having a structured light detecting function and including a laser projector, an eyeglass lens, at least one first diffractive optical element (DOE) film, an invisible light camera and a second DOE film are provided. The laser projector is configured to emit at least one invisible beam and an image beam. The at least one first DOE film is disposed on the eyeglass lens. The first DOE film is configured to diffract the invisible beam into a structured beam. The structured beam is transmitted to an object to be detected, so as to form a light pattern on the object to be detected. The invisible light camera is configured to photograph the light pattern on the object to be detected. The second DOE film is disposed on the eyeglass lens, and is configured to make the image beam travel to an eye.

15 Claims, 8 Drawing Sheets

(56) References Cited

U.S. PATENT DOCUMENTS

| | | | |
|---|---|---|---|
| 2018/0299680 A1 | 10/2018 | Alexander et al. | |
| 2018/0321495 A1* | 11/2018 | Andrews | H04N 9/3164 |
| 2020/0249483 A1* | 8/2020 | Nicholson | G02B 26/101 |
| 2021/0247612 A1* | 8/2021 | Hudman | G02B 6/005 |

FOREIGN PATENT DOCUMENTS

| | | |
|---|---|---|
| CN | 105676454 | 8/2019 |
| TW | 202018369 | 5/2020 |
| WO | 2017037708 | 3/2017 |

* cited by examiner

AUGMENTED REALITY EYEGLASSES HAVING STRUCTURED LIGHT DETECTING FUNCTION

CROSS-REFERENCE TO RELATED APPLICATION

This application claims the priority benefit of Taiwan application no. 109132019, filed on Sep. 17, 2020. The entirety of the above-mentioned patent application is hereby incorporated by reference herein and made a part of this specification.

TECHNICAL FIELD

The invention relates to an augmented reality display, and more particularly, relates to augmented reality eyeglasses having a structured light detecting function.

BACKGROUND

With the advancement of display technology, virtual reality display technology and augmented reality display technology have gradually become popular and have been fully researched and developed. The virtual reality display technology allows users to be immersed in the virtual world displayed on the display, and can display three-dimensional images. The augmented reality display technology allows users to see images of the virtual world in addition to objects in the real world, and even enables the images of the virtual world to interact with the objects in the real world.

When the display provides an image of the virtual world (i.e., a virtual image) to the user's eyes, if the system can know a position and a rotation angle of the eye, the corresponding virtual image with a better display effect may then be provided. However, when an eye tracker is added to an augmented reality display device, there are disadvantages of too many components and an overly complex system.

SUMMARY

The invention provides augmented reality eyeglasses having a structured light detecting function, which integrate light sources of a structured light into a laser projector for displaying images. Therefore, a simpler structure with a smaller number of components may be achieved.

An embodiment of the invention provides augmented reality eyeglasses having a structured light detecting function, which are adapted to be worn in front of an eye. The augmented reality eyeglasses having the structured light detecting function include a laser projector, an eyeglass lens, at least one first diffractive optical element, an invisible light camera and a second diffractive optical element film. The laser projector is configured to emit at least one invisible beam and an image beam. The eyeglass lens is disposed on paths of the invisible beam and the image beam. The at least one first diffractive optical element film is disposed on the eyeglass lens and located on the path of the invisible beam. The first diffractive optical element film is configured to diffract the invisible beam into a structured beam. The structured beam is transmitted to an object to be detected, so as to form a light pattern on the object to be detected. The invisible light camera is configured to photograph the light pattern on the object to be detected. The second diffractive optical element film is disposed on the eyeglass lens and located on the path of the image beam. The second diffractive optical element film is configured to make the image beam travel to the eye.

In the augmented reality eyeglasses having the structured light detecting function according to the embodiments of the invention, the laser projector not only emits the image beam, but also emits the invisible beam. The invisible beam is diffracted by the first diffractive optical element film to form the structured beam, which is used to detect the object to be detected. In other words, according to the embodiments of the invention, the light sources of the structured light are integrated into the laser projector for displaying images. Therefore, the augmented reality eyeglasses having the structured light detecting function can have a simpler structure with a smaller number of components while achieving the function of displaying images and detecting the object to be detected.

DETAILED DESCRIPTION

Figure 1:
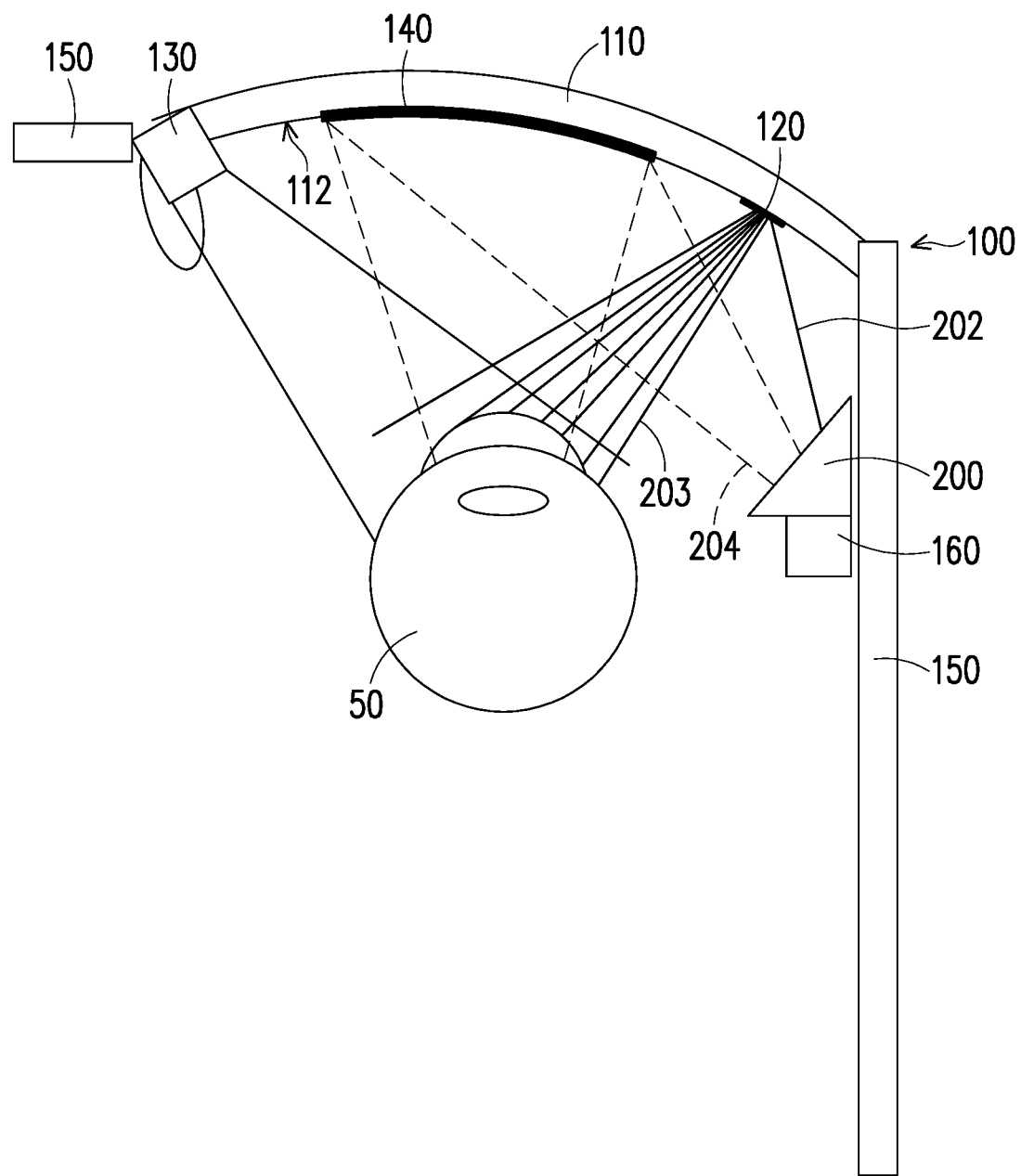
FIG. 1 is a schematic diagram of an optical path of augmented reality eyeglasses having a structured light detecting function according to an embodiment of the invention.
Figure 2:
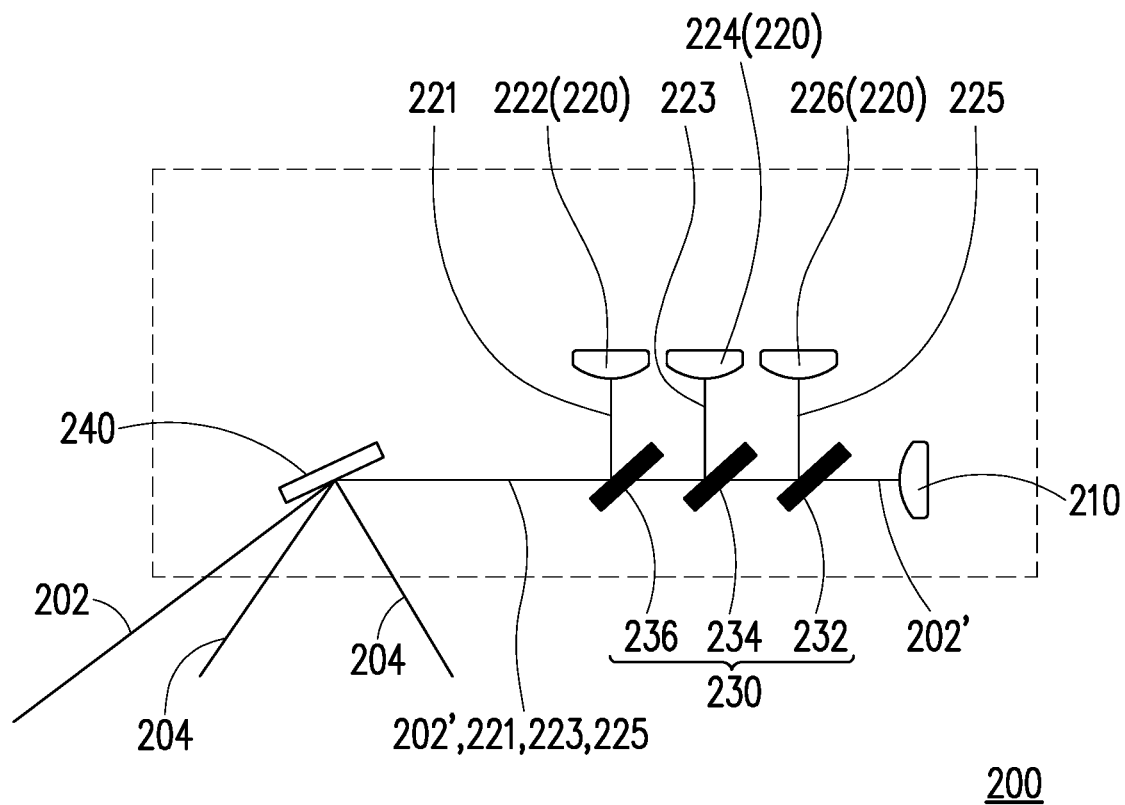
FIG. 2 is a schematic diagram of an optical path of a laser projector in FIG. 1.
Figure 3:
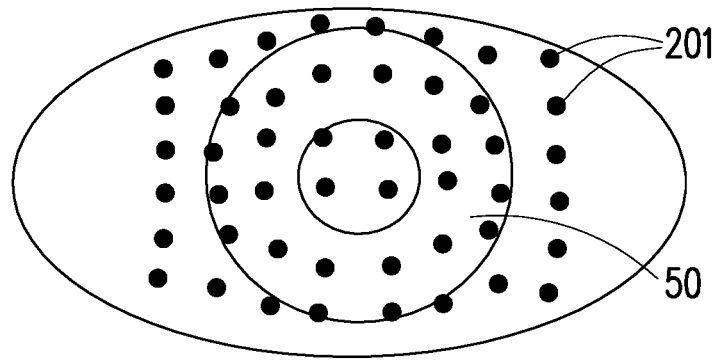
FIG. 3 is a schematic diagram of a light pattern formed on an eye by a structured light of FIG. 1.

FIG. 1 is a schematic diagram of an optical path of augmented reality eyeglasses having a structured light detecting function according to an embodiment of the invention. FIG. 2 is a schematic diagram of an optical path of a laser projector in FIG. 1. FIG. 3 is a schematic diagram of a light pattern formed on an eye by a structured light of FIG. 1. Referring to FIG. 1 to FIG. 3, augmented reality eyeglasses 100 having a structured light detecting function of the present embodiment are adapted to be worn in front of an eye 50. The augmented reality eyeglasses 100 having the structured light detecting function include a laser projector 200, an eyeglass lens 110, at least one first diffractive optical element film (one first diffractive optical element film 120 is illustrated in FIG. 1 as an example), an invisible light camera 130 and a second diffractive optical element film 140. The laser projector 200 is configured to emit at least one invisible beam 202 (one invisible beam 202 is illustrated in FIG. 1 as an example) and an image beam 204. The eyeglass lens 110 is disposed on paths of the invisible beam 202 and the image beam 204. The first diffractive optical element film 120 is disposed on the eyeglass lens 110 and located on the path of the invisible beam 202. The first diffractive optical element film 120 is configured to diffract the invisible beam 202 into a structured beam 203. This diffraction is, for example, reflective type diffraction. The structured beam 203 is transmitted to an object to be detected, so as to form a light pattern on the object to be detected. In this embodiment, the object to be detected is the eye 50, and the structured beam 203 forms a light pattern 201 on the eye 50.

The invisible light camera 130 is configured to photograph the light pattern 201 on the object to be detected. The second diffractive optical element film 140 is disposed on the eyeglass lens 110 and located on the path of the image beam 204. The second diffractive optical element film 140 is configured to transmit the image beam 204 to the eye 50 (e.g., to diffract it to the eye 50) so that the eye 50 can see an image frame to be displayed by the laser projector 200 (which is presented as a virtual image located in front of the eyes 50). The diffraction of the image beam 204 by the second diffractive optical element film 140 is, for example, reflective type diffraction. Further, in this embodiment, the first diffractive optical element film 120 and the second diffractive optical element film 140 are disposed on a surface 112 of the eyeglass lens 110 facing the eye 50. In addition, the second diffractive optical element film140 may be a general diffractive optical element film or a holographic optical element (HOE) film.

In this embodiment, the laser projector includes an infrared laser source 210, a plurality of laser sources 220 of different colors, a light combining module 230 and a scanning mirror 240. The infrared laser source 210 is configured to emit an infrared beam 202'. These laser sources 220 of different colors are configured to emit a plurality of beams of different colors. In this embodiment, these laser sources 220 of different colors include a red laser source 222, a green laser source 224 and a blue laser source 226, respectively emitting a red beam 221, a green beam 223 and a blue beam 225. In this embodiment, the infrared laser source 210 and these laser sources 220 of different colors are all laser diodes, and the beams emitted by them are laser beams.

The light combining module 230 is disposed on paths of the infrared beam 202' and these beams of different colors (e.g., the red beam 221, the green beam 223 and the blue beam 225) to combine the paths of the infrared beam and the beams of different colors. The scanning mirror 240 is disposed on the paths of the infrared beam 202' and these beams of different colors from the light combining module 230. The scanning mirror 240 is adapted to rotate so that the infrared beam 202' forms the invisible beam 202 irradiated on the first diffractive optical element film 120 and these beams of different colors form the image beam 204 scanning on the second diffractive optical element film 140. Further, in this embodiment, the invisible light camera 130 is, for example, an infrared camera.

Figure 4:
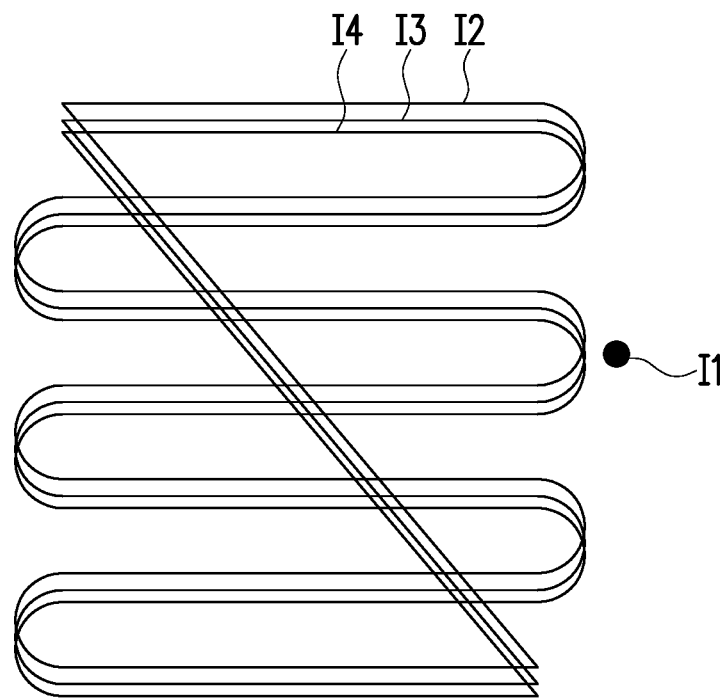
FIG. 4 shows scanning paths and positions of a red beam, a green beam, a blue beam and an infrared beam of FIG. 2 on an eyeglass lens.

FIG. 4 shows scanning paths and positions of a red beam, a green beam, a blue beam and an infrared beam of FIG. 2 on an eyeglass lens. Referring to FIG. 1, FIG. 2 and FIG. 4, by the rotation of the scanning mirror 240, the infrared laser source 210 can emit the infrared beam 202' when the scanning mirror 240 is rotated to a proper angle, and yet these laser sources 220 different colors do not emit the red beam 221, the green beam 223 and the blue beam 225 at the time. At this time, the infrared beam 202' is the invisible beam 202 irradiated on the first diffractive optical element film 120 and forms a light spot I1 on the first diffractive optical element film 120. Then, the first diffractive optical element film 120 diffracts the infrared beam 202' into the structured beam 203. In addition, during most of the other time, the scanning mirror 240 continuously rotates at other angles At this time, these laser sources 220 of different colors can emit the red beam 221, the green beam 223 and the blue beam 225, while the infrared laser source 210 does not emit the infrared beam 202'. Accordingly, the red beam 221, the green beam 223 and the blue beam 225 can respectively form a red light scanning path 12, a green light scanning path 13 and a blue light scanning path 14 on the second diffractive optical element film 140. In addition, with the continuous rotation of the scanning mirror 240, respective intensities of the red beam 221, the green beam 223 and the blue beam 225 can be continuously changed, so that colors and brightness of these scanning paths can be changed. The second diffractive optical element film 140 then diffracts the red beam 221, the green beam 223 and the blue beam 225 to the eye 50, so that the eye 50 can see a color image frame.

In addition to the color image frame, the eyes 50 can also see the outside scenery through the eyeglass lens 110 to achieve the effect of augmented reality. The eyeglass lens 110 is, for example, a myopia eyeglass lens, a hyperopia eyeglass lens, a presbyopia eyeglass lens or a plain eyeglass lens.

In this embodiment, the light combining module 230 may include a plurality of dichroic mirrors or a plurality of dichroic prisms. For instance, the light combining module 230 includes a dichroic mirror 232, a dichroic mirror 234, and a dichroic mirror 236. The dichroic mirror 232 is adapted to allow the infrared beam 202' to pass and travel to the dichroic mirror 234, and the dichroic mirror 232 is adapted to reflect the blue beam 225 to the dichroic mirror 234. The dichroic mirror 234 is adapted to allow the infrared beam 202' and the blue beam 225 to pass and travel to the dichroic mirror 236, and the dichroic mirror 234 is adapted to reflect the green beam 223 to the dichroic mirror 236. The dichroic mirror 236 is adapted to allow the infrared beam 202', the blue beam 225 and the green beam 223 to pass and travel to the scanning mirror 240, and the dichroic mirror 236 is adapted to reflect the red beam 221 to the scanning mirror 240. In this way, the light combining module 230 can combine the paths of the red beam 221, the green beam 223, the blue beam 225 and the infrared beam 202'.

In this embodiment, the augmented reality eyeglasses 100 having the structured light detecting function further include an eyeglass frame 150. The laser projector 200, the eyeglass lens 110 and the invisible light camera 130 are disposed on the eyeglass frame 150. The laser projector 200 may be disposed on the temples of the eyeglass frame 150, and the invisible light camera 130 can be disposed on the center of the eyeglass frame 150 near the nose pad. Further, in this embodiment, the augmented reality eyeglasses 100 having the structured light detecting function further include a processor 160, which is electrically connected to the invisible light camera 130, and configured to calculate a position of the object to be detected (i.e., the eye 50 in this embodiment) according to the light pattern 201 (as illustrated in FIG. 3) photographed by the invisible light camera 130 (e.g., to calculate a position and a gaze direction of the eye 50). Since the light pattern 201 will have deformation or shift along with the concave-convex curved surface of the eye 50, the processor 160 can calculate the position of the eye in three-dimensional space based on the deformation or shift. The processor 160 may also be configured on the eyeglass frame 150, for example, on the temples of the eyeglass frame 150.

In an embodiment, the processor 160 is, for example, a central processing unit (CPU), a microprocessor, a digital signal processor (DSP), a programmable controller, a programmable logic device (PLD) or other similar devices or a combination of these devices, which are not particularly limited by the invention. Further, in an embodiment, various functions of the processor 160 may be implemented as a plurality of program codes. These program codes will be stored in one memory so the program codes executed by the processor 160 later. Alternatively, in an embodiment, various functions of the processor 160 may be implemented as one or more circuits. The invention is not intended to limit whether various functions of the processor 160 are implemented by ways of software or hardware.

In the augmented reality eyeglasses 100 having the structured light detecting function of this embodiment, the laser projector 200 not only emits the image beam 204, but also emits the invisible beam 202. The invisible beam 202 is diffracted by the first diffractive optical element film 120 to form the structured beam 203, which is used to detect the object to be detected. In other words, in this embodiment, the light sources of the structured light 203 are integrated into the laser projector 200 for displaying images. That is to say, the light sources of an eye tracker are integrated into the laser projector 200. Therefore, the augmented reality eyeglasses 100 having the structured light detecting function can have a simpler structure with a smaller number of components while achieving the function of displaying images and detecting the object to be detected.

Figure 5:
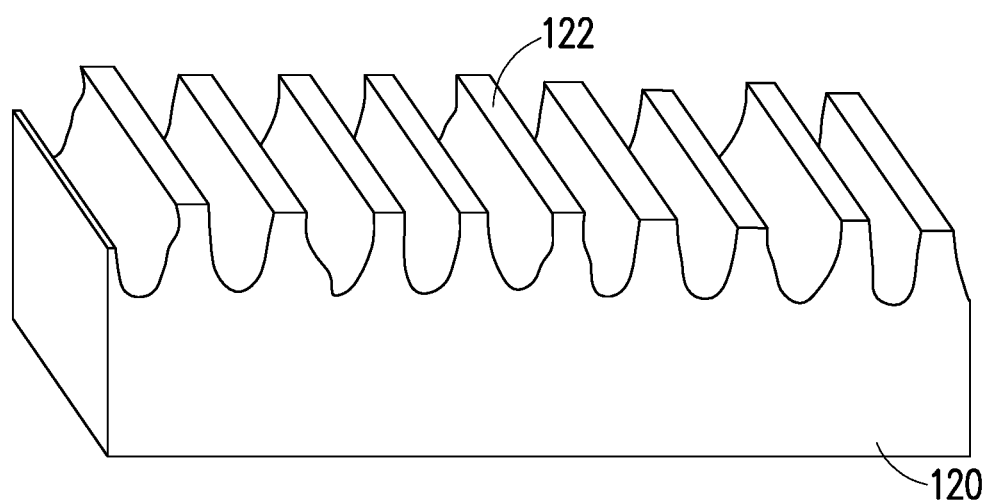
FIG. 5 is a 3D view of an embodiment of the first diffractive optical element film in FIG. 1.
Figure 6:
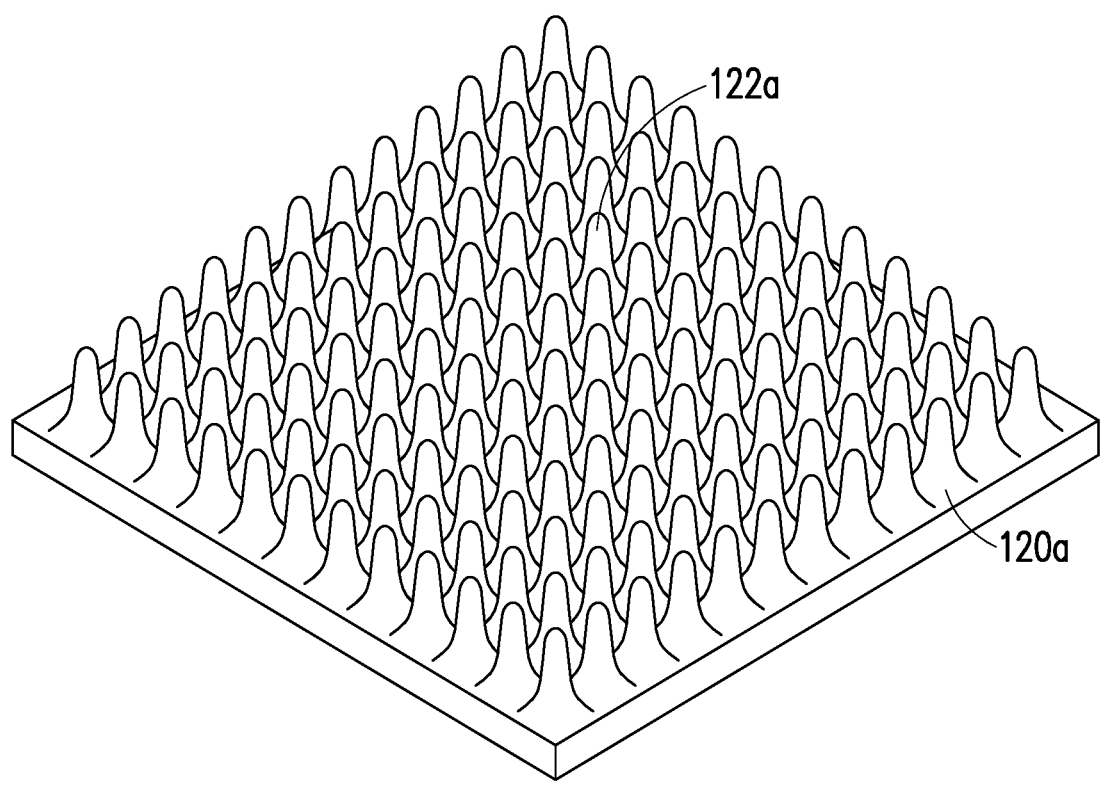
FIG. 6 is a 3D view of another embodiment of the first diffractive optical element film in FIG. 1.

FIG. 5 is a 3D view of an embodiment of the first diffractive optical element film in FIG. 1, and FIG. 6 is a 3D view of another embodiment of the first diffractive optical element film in FIG. 1. Referring to FIG. 1 and FIG. 5, the first diffractive optical element film 120 may have a plurality of microstructures 122, such as strip-shaped protrusions in FIG. 5. Each of the microstructures 122 can extend in a direction perpendicular to the plane of FIG. 1, and the microstructures 122 can be arranged along the horizontal direction of FIG. 1. The light pattern generated in this way is, for example, a striped light pattern. Referring to FIG. 1 and FIG. 6, in another embodiment, a first diffractive optical element film 120a of FIG. 6 may be used instead of the first diffractive optical element film 120 of FIG. 5. The first diffractive optical element film 120a of FIG. 6 has a plurality of microstructures 122a arranged in two dimensions. These microstructures 122a are, for example, dot-shaped protrusions. The light pattern generated in this way includes, for example, dot-shaped light patterns 201 arranged in an array as shown in FIG. 3. The first diffractive optical element film 120 of FIG. 5 and the first diffractive optical element film 120a of FIG. 6 are, for example, diffraction gratings.

Figure 7:
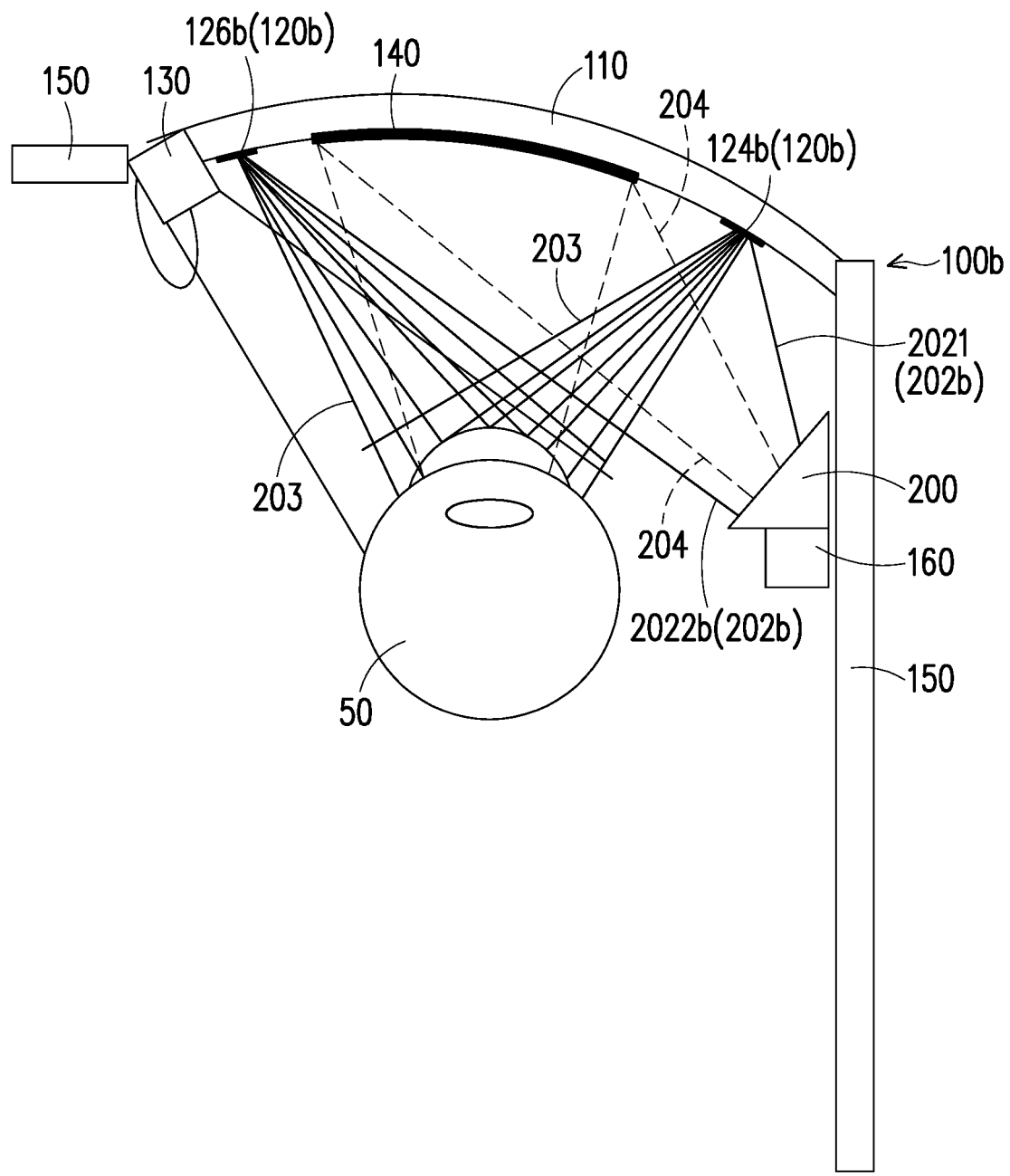
FIG. 7 is a schematic diagram of an optical path of augmented reality eyeglasses having a structured light detecting function according to another embodiment of the invention.
Figure 8:
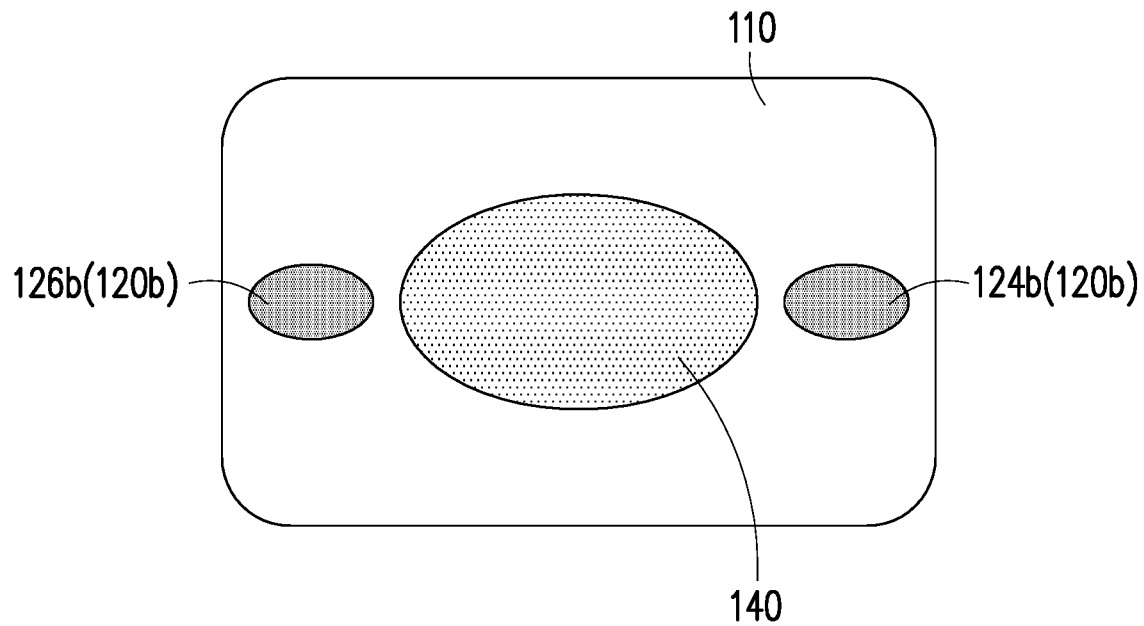
FIG. 8 is a front view of the eyeglass lens in FIG. 7 viewed from a line of sight of the eye.
Figure 9:
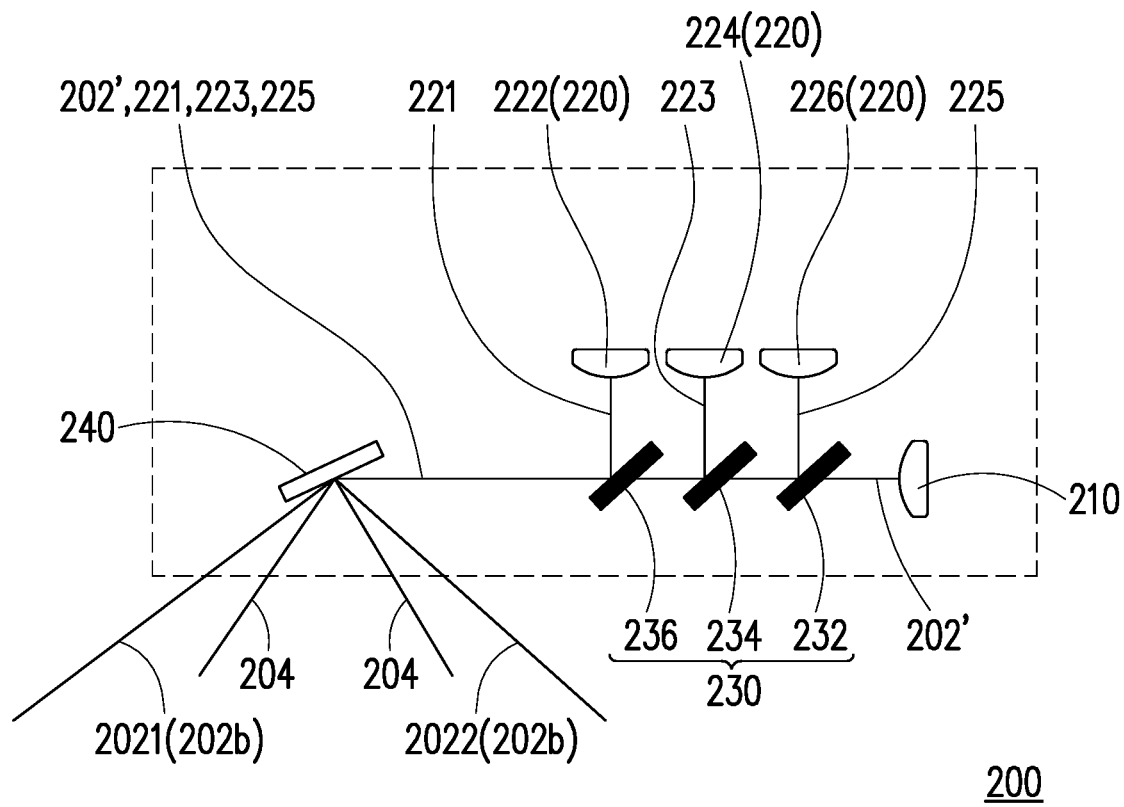
FIG. 9 is a schematic diagram of an optical path of a laser projector in FIG. 7.

FIG. 7 is a schematic diagram of an optical path of augmented reality eyeglasses having a structured light detecting function according to another embodiment of the invention. FIG. 8 is a front view of the eyeglass lens in FIG. 7 viewed from a line of sight of the eye. FIG. 9 is a schematic diagram of an optical path of a laser projector in FIG. 7. Referring to FIG. 7 to FIG. 9, augmented reality eyeglasses 100b having a structured light detecting function of the present embodiment are similar to the augmented reality eyeglasses 100 having the structured light detecting function of FIG. 1, and the main differences between the two are as follows. The augmented reality eyeglasses 100b having the structured light detecting function of this embodiment include two first diffractive optical element films 120b respectively disposed on two sides of the second diffractive optical element film 140 (e.g., a first diffractive optical element film 124b located on the right side of the second diffractive optical element film 140 and a first diffractive optical element film 126b located on the left side of the second diffractive optical element film 140). In addition, when the scanning mirror 240 of the laser projector 200 turns to two different angles at different times, the infrared laser source 210 emits the infrared beam 202', and the scanning mirror 240 at two different angles reflects the infrared beam 202' to different directions at two different times to form two invisible beams 202b transmitted in different directions (e.g., an invisible beam 2021 and an invisible beam 2022). The invisible beam 2021 is irradiated on the first diffractive optical element film 124b to form a structured beam 203. The invisible beam 2022 is irradiated on the first diffractive optical element film 126b to form another structured beam 203. The two structured beams 203 are both transmitted to the eye 50 to form two light patterns on the eye. The two light patterns can cover more angles of the eye 50, so that the processor 160 can be more accurate in calculating the position and the gaze direction of the eye 50.

Figure 10:
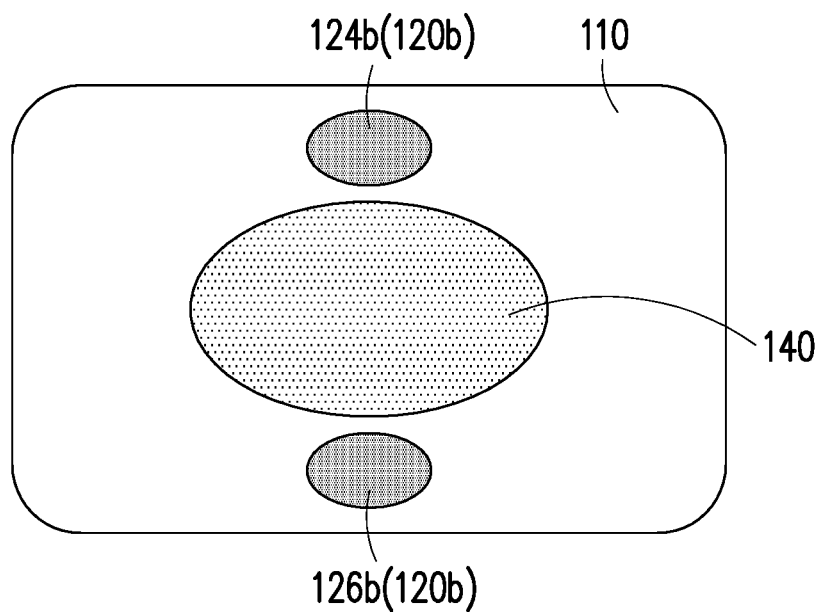
FIG. 10 is a front view of an eyeglass lens in augmented reality eyeglasses having a structured light detecting function according to another embodiment viewed from a line of sight of the eye.

FIG. 10 is a front view of an eyeglass lens in augmented reality eyeglasses having a structured light detecting function according to another embodiment viewed from a line of sight of the eye. Referring to FIG. 7, FIG. 8 and FIG. 10, augmented reality eyeglasses having a structured light detecting function in the embodiment of FIG. 10 are similar to the augmented reality eyeglasses 100b having the structured light detecting function of FIG. 7, and the differences between the two are as follows. The first diffractive optical element film 124b and the first diffractive optical element film 126b in the embodiment of FIG. 10 are respectively disposed on the upper and lower sides of the second diffractive optical element film 140. The invisible beam 2021 and the invisible beam 2022 are respectively irradiated on the first diffractive optical element film 124b and the first diffractive optical element film 126b.

Figure 11:
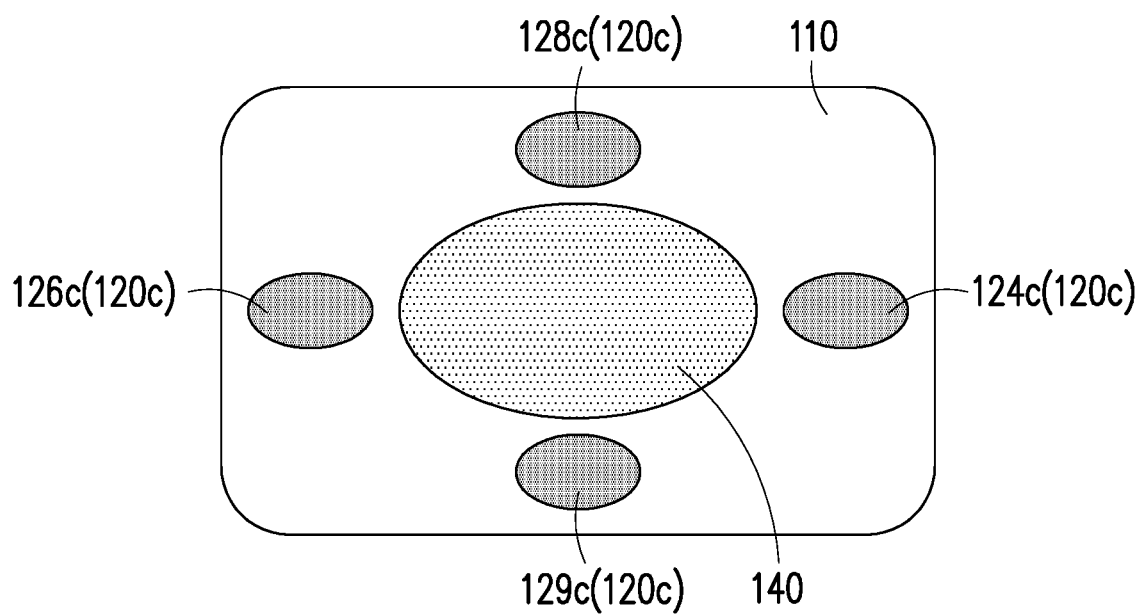
FIG. 11 is a front view of an eyeglass lens in augmented reality eyeglasses having a structured light detecting function according to yet another embodiment viewed from a line of sight of the eye.

FIG. 11 is a front view of an eyeglass lens in augmented reality eyeglasses having a structured light detecting function according to yet another embodiment viewed from a line of sight of the eye. Referring to FIG. 7, FIG. 8 and FIG. 11, augmented reality eyeglasses having a structured light detecting function in the embodiment of FIG. 11 are similar to the augmented reality eyeglasses 100b having the structured light detecting function of FIG. 7, and the differences between the two are as follows. The augmented reality eyeglasses having the structured light detecting function in the embodiment of FIG. 11 include four first diffractive optical element films 120c disposed around the second diffractive optical element film 140 (e.g., first diffractive optical element films 124c, 126c, 128c and 129c respectively disposed on the right, left, upper and lower sides of the second diffractive optical element film 140). The scanning mirror of the laser projector rotates to four different angles at four different times to reflect the infrared beam in four different directions to form four invisible beams respectively irradiated on the first diffractive optical element films 124c, 126c, 128c and 129c. The first diffractive optical element films 124c, 126c, 128c and 129c diffract the four invisible beams into four structured beams. The four structured beams are all transmitted to the eye 50 to form four light patterns on the eye. The four light patterns can cover more angles of the eye 50, so that the processor 160 can be more accurate in calculating the position and the gaze direction of the eye 50.

Figure 12:
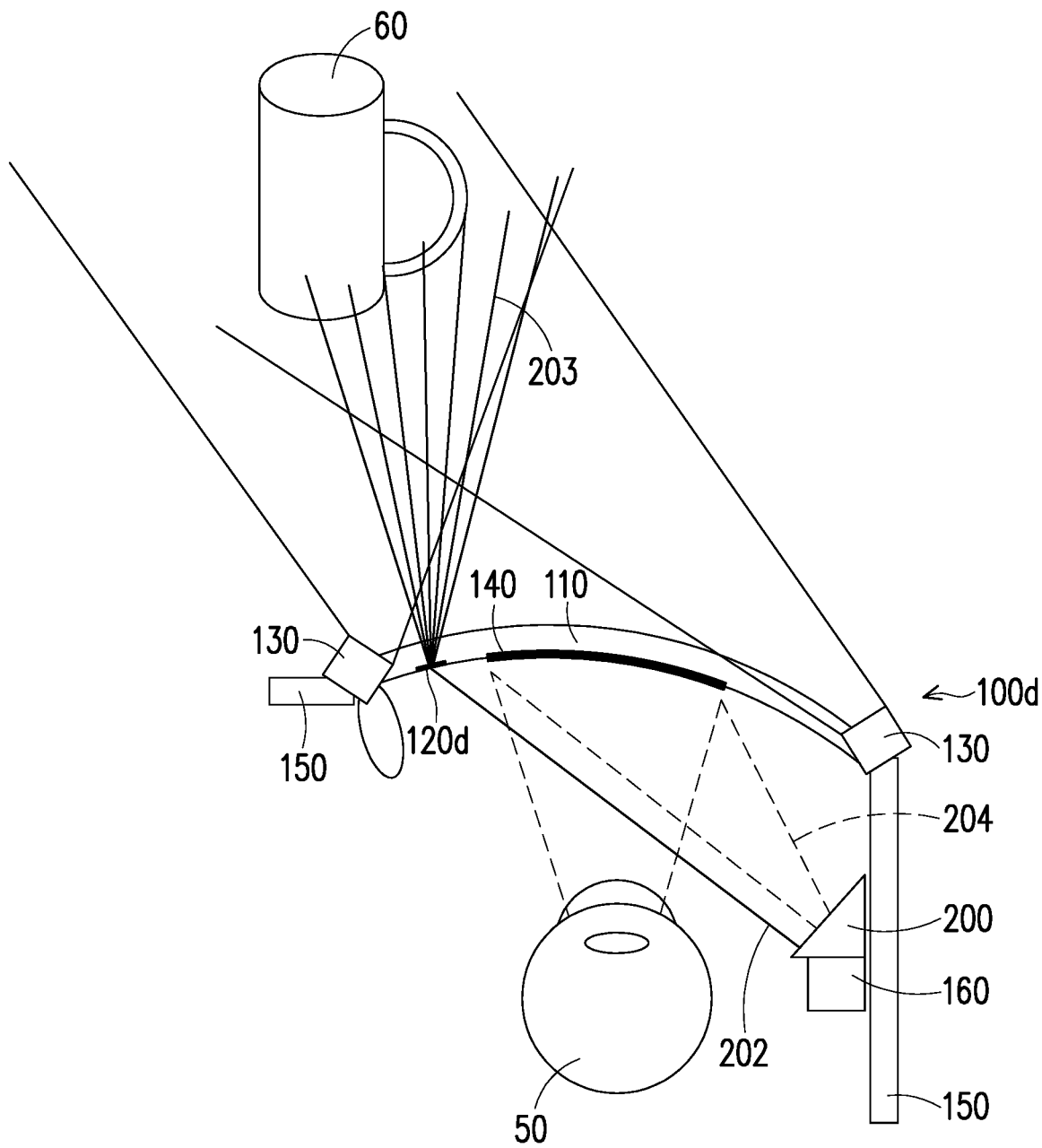
FIG. 12 is a schematic diagram of an optical path of augmented reality eyeglasses having a structured light detecting function according to another embodiment of the invention.

FIG. 12 is a schematic diagram of an optical path of augmented reality eyeglasses having a structured light detecting function according to another embodiment of the invention. Referring to FIG. 12, augmented reality eyeglasses 100d having a structured light detecting function of the present embodiment are similar to the augmented reality eyeglasses 100 having the structured light detecting function of FIG. 1, and the differences between the two are as follows. In the augmented reality eyeglasses 100d having the structured light detecting function of the present embodiment, the object to be detected is an external object 60. The eyeglass lens 110 is located between the external object 60 and the eye 50. In addition, a first diffractive optical element film 120d diffracts the invisible beam 202 toward the outside into a structured beam 203. This diffraction is, for example, transmissive type diffraction. The structured beam 203 is transmitted to the external object 60, so as to form a light pattern on the external object 60. By photographing the light pattern using the invisible light camera 130, the processor 160 can calculate a position of the external object 60. In this embodiment, there may be multiple invisible light cameras 130, such as two, which are respectively disposed at the center and one side of the eyeglass frame 150. However, the invention does not limit the number of invisible light cameras 130. In another embodiment, the number of the invisible light cameras 130 may also be one.

To sum up, in the augmented reality eyeglasses having the structured light detecting function according to the embodiments of the invention, the laser projector not only emits the image beam, but also emits the invisible beam. The invisible beam is diffracted by the first diffractive optical element film to form the structured beam, which is used to detect the object to be detected. In other words, according to the embodiments of the invention, the light sources of the structured light are integrated into the laser projector for displaying images. Therefore, the augmented reality eyeglasses having the structured light detecting function can have a simpler structure with a smaller number of components while achieving the function of displaying images and detecting the object to be detected.

The invention claimed is:

1. Augmented reality eyeglasses having a structured light detecting function, adapted to be worn in front of an eye, the augmented reality eyeglasses having the structured light detecting function comprising:
a laser projector, configured to emit at least one invisible beam and an image beam;
an eyeglass lens, disposed on paths of the invisible beam and the image beam;
at least one first diffractive optical element film, disposed on the eyeglass lens and located on the path of the invisible beam, the first diffractive optical element film being configured to diffract the invisible beam into a structured beam, wherein the structured beam is transmitted to an object to be detected, so as to form a light pattern on the object to be detected;
an invisible light camera, configured to photograph the light pattern on the object to be detected; and
a second diffractive optical element film, disposed on the eyeglass lens and located on the path of the image beam, the second diffractive optical element film being separated from the at least one first diffractive optical element film and being configured to make the image beam travel to the eye.

2. The augmented reality eyeglasses having the structured light detecting function of claim 1, wherein the object to be detected is the eye.

3. The augmented reality eyeglasses having the structured light detecting function of claim 1, wherein the object to be detected is an external object, wherein the eyeglass lens is located between the external object and the eye.

4. The augmented reality eyeglasses having the structured light detecting function of claim 1, wherein the first diffractive optical element film and the second diffractive optical element film are disposed on a surface of the eyeglass lens facing the eye.

5. The augmented reality eyeglasses having the structured light detecting function of claim 1, wherein the laser projector comprises:
an infrared laser source, configured to emit an infrared beam;
a plurality of laser sources of different colors, configured to emit a plurality of beams of different colors;
a light combining module, disposed on paths of the infrared beam and the beams of different colors to combine the paths of the infrared beam and the beams of different colors; and
a scanning mirror, disposed on the paths of the infrared beam and the beams of different colors from the light combining module, wherein the scanning mirror is adapted to rotate so that the infrared beam forms the at least one invisible beam irradiated on the at least one first diffractive optical element film and the beams of different colors form the image beam scanning on the second diffractive optical element film.

6. The augmented reality eyeglasses having the structured light detecting function of claim 5, wherein the light combining module comprises a plurality of dichroic mirrors or a plurality of dichroic prisms.

7. The augmented reality eyeglasses having the structured light detecting function of claim 5, wherein the beams of different colors comprises a red beam, a green beam, and a blue beam.

8. The augmented reality eyeglasses having the structured light detecting function of claim 1, wherein the at least first diffractive optical element film is two first diffractive optical element films respectively disposed on two sides of the second diffractive optical element film, and the at least one invisible beam is two invisible beams respectively irradiated on the two first diffractive optical element films.

9. The augmented reality eyeglasses having the structured light detecting function of claim 1, wherein the at least first diffractive optical element film is four first diffractive optical element films respectively disposed around the second diffractive optical element film, and the at least one invisible beam is four invisible beams respectively irradiated on the four first diffractive optical element films.

10. The augmented reality eyeglasses having the structured light detecting function of claim 1, wherein the second diffractive optical element film is a holographic optical element film.

11. The augmented reality eyeglasses having the structured light detecting function of claim 1, further comprising:
a processor, electrically connected to the invisible light camera, and configured to calculate a position of the object to be detected according to the light pattern photographed by the invisible light camera.

12. The augmented reality eyeglasses having the structured light detecting function of claim 1, further comprising: an eyeglass frame, wherein the laser projector and the eyeglass lens are disposed on the eyeglass frame.

13. The augmented reality eyeglasses having the structured light detecting function of claim 1, wherein the eyeglass lens is a myopia eyeglass lens, a hyperopia eyeglass lens, a presbyopia eyeglass lens or a plain eyeglass lens.

14. The augmented reality eyeglasses having the structured light detecting function of claim 1, wherein the invisible beam is an infrared beam.

15. The augmented reality eyeglasses having the structured light detecting function of claim 1, wherein the eye is capable of see outside scenery through the eyeglass lens to achieve an effect of augmented reality.

\* \* \* \* \*